US011107561B2

(12) United States Patent
Matthieu et al.

(10) Patent No.: US 11,107,561 B2
(45) Date of Patent: Aug. 31, 2021

(54) CLOUD-BASED DISTRIBUTED HEALTHCARE SYSTEM WITH BIOMETRIC DEVICES AND ASSOCIATED METHODS

(71) Applicant: Citrix Systems, Inc., Fort Lauderdale, FL (US)

(72) Inventors: Chris Matthieu, Tempe, AZ (US); Darcíe Tuuri, Santa Clara, CA (US); Steve Wilson, Santa Clara, CA (US)

(73) Assignee: CITRIX SYSTEMS , INC., Fort Lauderdale, FL (US)

( * ) Notice: Subject to any disclaimer, the term of this patent is extended or adjusted under 35 U.S.C. 154(b) by 610 days.

(21) Appl. No.: 15/581,696

(22) Filed: Apr. 28, 2017

(65) Prior Publication Data

US 2018/0314800 A1    Nov. 1, 2018

(51) Int. Cl.
*G16H 10/60* (2018.01)
*H04L 29/06* (2006.01)
(Continued)

(52) U.S. Cl.
CPC ......... *G16H 10/60* (2018.01); *G06F 21/6245* (2013.01); *G16H 40/67* (2018.01);
(Continued)

(58) Field of Classification Search
CPC ........ G16H 10/60; G16H 50/20; G16H 50/70; G16H 50/50; G16H 40/67; G16H 20/30; G16H 40/63; G16H 50/30; G16H 50/00; G16H 15/00; G16H 40/60; H04L 63/0428; G06F 21/6245; G06F 19/00; G06Q 2220/10
See application file for complete search history.

(56) References Cited

U.S. PATENT DOCUMENTS

2008/0004904 A1\* 1/2008 Tran ..................... A61B 5/0022
705/2
2008/0269625 A1\* 10/2008 Halperin .................. A61B 5/08
600/508
(Continued)

FOREIGN PATENT DOCUMENTS

AU    2016101455 A4 \* 9/2016

*Primary Examiner* — Joseph D Burgess
(74) *Attorney, Agent, or Firm* — Allen, Dyer, Doppelt + Gilchrist, PA

(57) ABSTRACT

A system includes biometric devices generating biometric data on a person, with the biometric devices transmitting the biometric data via respective messaging protocols. A messaging platform receives the biometric data from the biometric devices based on the respective messaging protocols. A biometric data server receives the biometric data from the messaging platform. The biometric data server includes a biometric database, a biometric data algorithm, and a biometric data analyzer. The biometric database is to store the biometric data. The biometric data algorithm is to generate a biometric data model over time based on the biometric data to determine the person's version of normal bio-feedback at any given time in comparison to other like time periods. The biometric data analyzer is to analyze new biometric data in view of the biometric data model, and to generate at least one caregiver notification alert when an anomaly is detected outside the biometric data model.

22 Claims, 4 Drawing Sheets

(51) Int. Cl.
    *G06F 21/62*    (2013.01)
    *G16H 50/50*    (2018.01)
    *G16H 50/70*    (2018.01)
    *G16H 40/67*    (2018.01)
    *G16H 50/20*    (2018.01)

(52) U.S. Cl.
    CPC ............ *G16H 50/20* (2018.01); *G16H 50/50* (2018.01); *G16H 50/70* (2018.01); *H04L 63/0428* (2013.01); *G06Q 2220/10* (2013.01)

(56) References Cited

U.S. PATENT DOCUMENTS

| | | | |
|---|---|---|---|
| 2016/0217259 A1* | 7/2016 | Chan | G16H 40/20 |
| 2016/0328577 A1* | 11/2016 | Howley | G06F 19/3475 |
| 2017/0155703 A1* | 6/2017 | Hao | H04L 67/12 |
| 2017/0212991 A1* | 7/2017 | Challapalli | G06F 19/00 |
| 2018/0000385 A1* | 1/2018 | Heaton | G08B 21/043 |
| 2018/0082036 A1* | 3/2018 | Hanrahan | G16H 10/60 |

* cited by examiner

CLOUD-BASED DISTRIBUTED HEALTHCARE SYSTEM WITH BIOMETRIC DEVICES AND ASSOCIATED METHODS

TECHNICAL FIELD

The present disclosure relates to healthcare management, and more particularly, to a cloud-based distributed healthcare system that aggregates and analyzes biometric data from disparate biometric devices, and related methods.

BACKGROUND

In today's healthcare world where specialties in medicine are abound, most patients see multiple doctors each calendar year, such as general practitioners, ophthalmologists, internists, obstetricians and countless others. When patients experience chronic illness, sudden diagnosis of disease, or simple family planning, the number of physicians can increase dramatically.

Lab work, body imaging scans, pharmacies and more, generate their own reporting outputs which are frequently sent to single physicians. Unfortunately, this information is not sent to other physicians who may be treating the same patients for other health issues. This collection of health care professionals often operates in silos, some owning private practices, others as part of larger health care groups that do not facilitate cross-company or intra-organization communications.

The burden of assimilating and assembling the data is left to each patient individually, some of whom will be unable to advocate for themselves from one specialist to the next. At best this creates and proliferates confusion for patients and their families; at worst, the result of physicians acting autonomously and unintentionally prescribing a course of treatment without all available data could potentially be catastrophic.

Add to this incredibly complex healthcare universe, a vast array of biometric monitoring devices are now available, allowing end-users instant access to personal statistics with a minute-by-minute snapshot of their current health. New technologies digitally measure and continually capture everything from the end-user's heart-rate and steps taken to a diabetic's current blood sugar levels. According to predictions, there will be 29.5B Internet of Things (IoT) devices worldwide by 2020. This is about 4 IoT devices per person.

SUMMARY

A system includes a plurality of biometric devices generating biometric data on a person, with the plurality of biometric devices transmitting the biometric data via respective messaging protocols. The system may further include a messaging platform and a biometric data server. The messaging platform may be configured to receive the biometric data from the plurality of biometric devices based on the respective messaging protocols. The biometric data server may be configured to receive the biometric data from the messaging platform, and includes a biometric database, a biometric data algorithm and a biometric analyzer.

The biometric data server may store the biometric data in the biometric database. The biometric data algorithm may generate a biometric data model over time based on the biometric data to determine the person's version of normal bio-feedback at any given time in comparison to other like time periods. The biometric data analyzer may analyze new biometric data in view of the biometric data model, and generates at least one caregiver notification alert when an anomaly is detected outside the biometric data model.

The biometric data server may be further configured to generate at least one permissions record identifying at least one caregiver allowed to receive the at least one caregiver notification alert. The at least one caregiver may have limited access to the biometric data based on the at least one permissions record.

The system may further comprise a controller to register the person, the plurality of biometric devices and at least one caregiver computing device with the messaging platform. The person, each biometric device and the at least one caregiver computing device may be assigned a respective universal unique identifier (MD) upon registration.

The biometric data server is further configured to transmit to the at least one caregiver computing device the biometric data from at least one of the plurality of biometric devices. The biometric data may be transmitted in real time. The biometric data may be encrypted before being transmitted.

The biometric data algorithm may comprise a machine learning algorithm. The biometric database may store the biometric data using a common data structure.

The system advantageously collects and aggregates a variety of bio-feedback data from a variety of disparate biometric devices and stores the bio-feedback data in a common format capable of conducting real-time, cross-system diagnostics. The biometric data algorithm advantageously determines each person's version of normal bio-feedbacks, predicts the onset of healthcare conditions and/or issues based on the biometric data model, and alerts caregivers of anomalies.

Another aspect is directed a method for operating a system as described above. The method comprises operating a messaging platform to receive the biometric data from the plurality of biometric devices based on the respective messaging protocols, and operating a biometric data server to receive the biometric data from the messaging platform. Operating the biometric data server includes storing the biometric data, operating a biometric data algorithm to generate a biometric data model over time based on the biometric data to determine the person's version of normal bio-feedback at any given time in comparison to other like time periods, and analyze new biometric data in view of the biometric data model and generate at least one caregiver notification alert when an anomaly is detected outside the biometric data model.

Yet another aspect is directed to a non-transitory computer readable medium for a system as described above. The non-transitory computer readable medium has a plurality of computer executable instructions for causing the system to perform steps comprising operating a biometric data server to store the biometric data in a biometric database, generate a biometric data model over time based on the biometric data to determine the person's version of normal bio-feedback at any given time in comparison to other like time periods, and analyze new biometric data in view of the biometric data model and generate at least one caregiver notification alert when an anomaly is detected outside the biometric data model.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
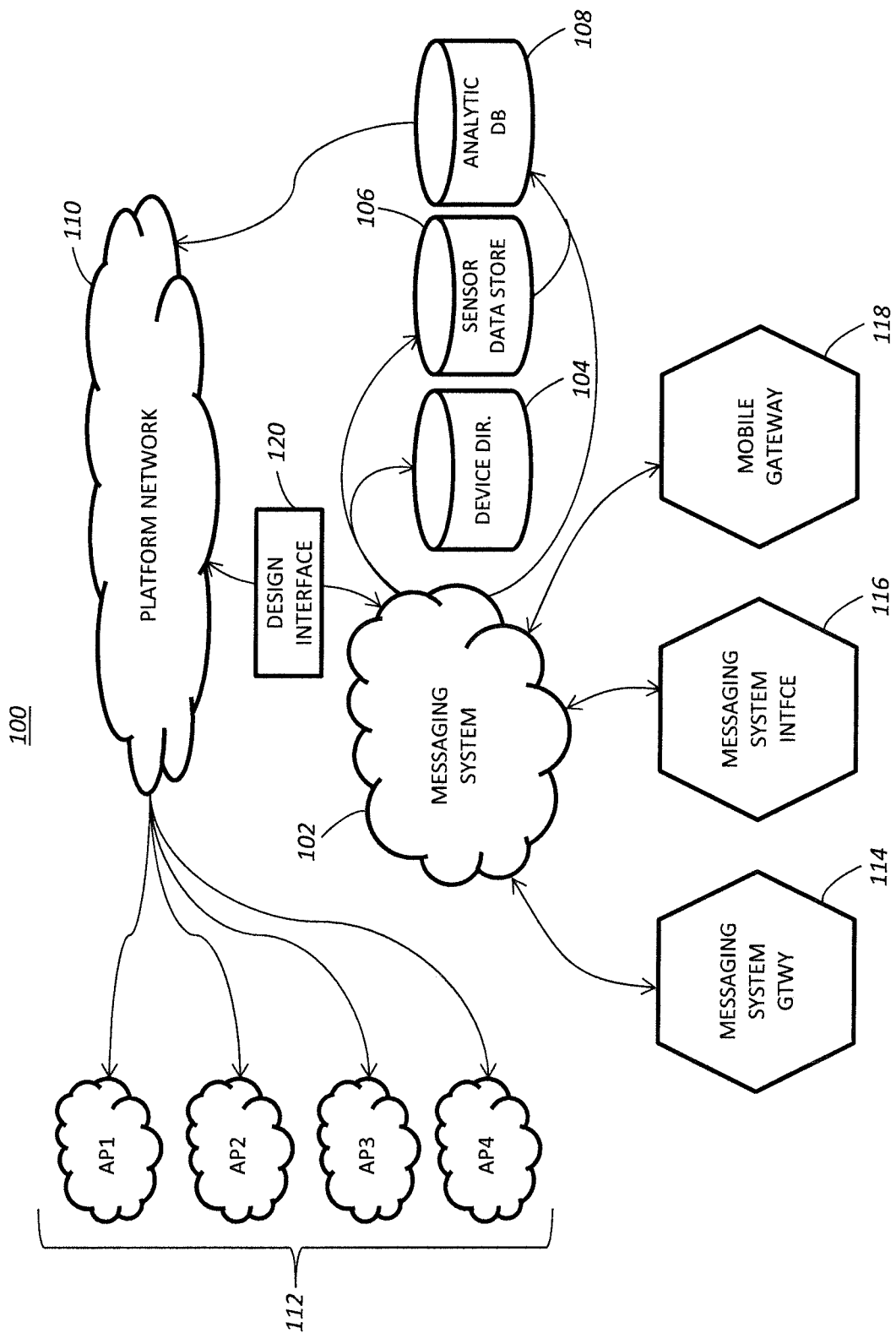
FIG. 1 is a block diagram of a system that supports a cross-protocol, machine-to-machine messaging platform.

Referring initially to FIG. 1, a system 100 that is a cross-protocol, machine-to-machine messaging platform will be discussed. The cross-protocol, machine-to-machine messaging platform advantageously provides a foundation for a cloud-based distributed healthcare system that aggregates and analyzes biometric data from disparate biometric devices for patients.

The illustrated system 100 allows Internet of Things (IoT) devices to communicate across different IoT messaging protocols. Support for the illustrated system 100 may also be found in U.S. Pat. No. 9,009,230. The '230 patent is assigned to the current assignee of the present application, and is incorporated herein by reference in its entirety.

An IoT device may include any network-connectable device or system having sensing or control functionality. In view of a cloud-based distributed healthcare system, an IoT device may function as a biometric device generating biometric data on a person. An IoT device may be connectable to a local area network (LAN), a personal area network (PAN), and to a wide area network (WAN). For example, an IoT device may include one or more radios operating using one or more communications protocols that allow the IoT device to connect to one or more LANs or PANs, such as WiFi™, ZigBee™, Bluetooth™, Bluetooth low Energy™ (BLE), Infrared Data Association, Transmission Control Protocol (TCP), User Datagram Protocol (UDP), and any other suitable protocol that allows connection to a LAN.

A LAN may interconnect various network devices and provide the network devices with the ability to connect to a WAN. A router, modem, access point, or other switching mechanism may be used to control and manage the connections to the network devices. A PAN may provide network access for a user's personal device (e.g., a network for connecting devices worn or carried by the user, for connecting devices located in the user's workspace, or the like), and may further provide access to other networks, such as a LAN or a WAN.

The IoT device may further include one or more radios that allow the IoT device to connect to a WAN, such as the Internet, a private cloud network, a public cloud network, or any other network external to a local network. In some embodiments, an IoT device may not include a cellular radio, and may only be connectable to a LAN, PAN, or WAN other than a cellular network. In some embodiments, an IoT device may include a cellular radio. The system 100 may also include third-party messaging services (e.g., Facebook, twitter, LinkedIn, SMS, etc.) as well as non-IoT devices and systems.

The system 100 may include one or more remote servers, or clouds, that are in communication with other devices or systems via a network, such as the Internet, an intranet, a LAN, a PAN, or a WAN. For example, the system 100 includes a common messaging system 102 (or messaging system or messaging platform 102) that supports machine-to-machine instant message exchange in real-time or near real-time. In some embodiments, the messaging system 102 may be an open source machine-to-machine messaging platform, enabling IoT devices, other devices or machines, and/or systems to exchange messages or otherwise communicate with any other IoT devices, other devices or machines, and/or systems.

The messaging system 102 may be implemented by one or more remote servers and may allow an IoT device, other device or machine, and/or a system to exchange communications or messages with another device or system regardless of whether the devices or systems are built by different manufacturers, operate using different connection protocols or interfaces, or whether the devices or systems are built with the ability to communicate with a network. While only a single messaging system 102 is shown in FIG. 1, one of ordinary skill in the art will appreciate that multiple private or public messaging systems may be implemented using the techniques described herein.

One or more remote servers of the messaging system 102 may be connected to a network via the Internet and/or other connection platforms (e.g., a WAN and/or a LAN) such that the servers may be accessed from anywhere in the world. The remote servers allow IoT devices, other devices or machines, and/or systems connected to the servers via the network to communicate and exchange messages with other IoT devices, other devices or machines, and/or systems from anywhere in the world. The remote servers may be configured with enough processing power to run an application, store and process data, and/or perform any other computing task. In some examples, the remote servers may provide enough processing power to operate applications running on devices located remotely from the servers, and applications running on the servers themselves.

Messaging system 102 may be configured to support multiple connection protocols, such as any suitable machine-to-machine connection protocol. For example, the messaging system 102 may support connection protocols such as hypertext transfer protocol (HTTP), websockets, message queuing telemetry transport (MQTT), constrained application protocol (CoAP), Extensible Messaging and Presence Protocol (XMPP), Simple Network Management Protocol (SNMP), AllJoyn, and/or any other suitable connection protocol. The multiple connection protocols supported by the messaging system 102 may be referred to herein as native connection protocols of the messaging system 102.

Messaging system 102 may also support multiple developer platforms, such as one or more software developer kits (SDKs). For example, the messaging system may support SDKs such as Node.JS, JavaScript, Python, Ruby, or any other suitable SDK. The support of multiple developer platforms and protocols provides programmers with the flexibility to customize functions, instructions, and commands for IoT devices, other devices or machines, and/or systems connected to messaging system 102.

The messaging system 102 may include a cloud infrastructure system that provides cloud services. In certain embodiments, services provided by the cloud infrastructure of messaging system 102 may include a host of services that are made available to users of the cloud infrastructure system on demand, such as registration, access control, and message routing for users, devices or machines, systems, or components thereof. Services provided by the messaging system 102 can be dynamically scaled to meet the demands of users.

The messaging system 102 may comprise one or more computers, servers, and/or systems. In some embodiments, the computers, servers, and/or systems that make up the cloud network of the messaging system 102 are different from a user's own on-premises computers, servers, and/or systems. For example, the cloud network may host an application, and a user may, via a communication network such as a WAN, LAN, and/or PAN, on demand, order and use the application.

In some embodiments, the cloud network of the messaging system 102 may host a Network Address Translation Traversal application to establish a secure connection between the messaging system 102 and a device or machine. A separate secure connection (e.g., using a native protocol of the messaging system 102) may be established by each device or machine for communicating with the messaging system 102. In certain embodiments, the cloud network of the messaging system 102 may include a suite of applications, middleware, or firmware that can be accessed by a user, device or machine, system, or component thereof.

Upon registering with the messaging system 102, each device or machine, person, and/or system may be assigned a unique identifier and a security token. For example, a device (IoT or other device) or system connected to the messaging system, a person associated with an account or an application that utilizes the messaging system, or the like may be assigned or otherwise provided with a distinct universally unique identifier (UUID) and/or a distinct security token.

Each IoT device, other device or machine, system, and/or person using a device must communicate its distinct UUID and security token to the messaging system 102 in order to access the messaging system 102. The messaging system 102 may authenticate the device, other device or machine, system, and/or person using each respective distinct UUID and token. The messaging system 102 may use the UUIDs to process, route, and/or otherwise manage messages and other communications to an appropriate device, person, system, and/or machine. For example, a device may send a message with its UUID and a destination UUID for the device, system, or person to which the message is destined. The messaging system 102 may process, route, and/or otherwise manage the message so that it is received at the appropriate destination.

In some embodiments, one or more components or programs of a device or system may also be assigned a unique identifier and a security token. In some cases, the unique identifier and/or token for the components of a device or system may be the same as the unique identifier and/or token of the device or system itself. In some cases, the unique identifier and/or token for a component or program of a device or system may be different from that of the device or system and may be unique only to the component or program.

In some embodiments, components of a device or system that may be assigned a unique identifier may include a sensor (e.g., a camera, motion sensor, temperature sensor, accelerometer, gyroscope, or any other available sensor), an output (e.g., a microphone, siren, display, light, tactile output, or any other available output), a third-party messaging service that the device or system is able to run, or any other component of a device or system that can be identified, accessed, and/or controlled.

Messaging system 102 may further be configured to interact with any application programming interface (API). Each API may also be assigned or otherwise provided with a unique identifier (e.g., a distinct UUID) and/or a security token. Assigning APIs with a unique identifier enables messaging system 102 to receive instructions from and provide instructions to any IoT device, other device or machine, and/or system that is connected to the messaging system 102. By being able to interact with any API, messaging system 102 may control the functionality of all components of a registered IoT device, other device or machine, and/or system that are accessible by the messaging system 102. In some embodiments, messaging system 102 may be configured such that a single message transmitted by messaging system 102 may be communicated to multiple devices and/or systems having different APIs.

Accessible IoT devices, other devices or machines, and/or systems include any device that has been registered with messaging system 102 and that has been assigned a unique identifier and/or a security token. For example, a user may purchase an IoT device. The user must register the IoT device with the messaging system 102, and may be assigned a UUID and security token by the messaging system 102 to make the IoT device accessible to the messaging system 102 and other devices registered with the messaging system 102.

Using the common messaging system 102, people, devices, systems, and/or components thereof that have assigned UUIDs can query and communicate with a network of other people, devices, system, and components thereof that have assigned UUIDs and that meet specific search criteria. For example, a device may query the common messaging system 102 searching for a specific type of device or devices that are located in a particular area, and may receive a list of UUIDs for devices that meet the search criteria. The device may then send a message with a destination UUID assigned to the destination device to which the device wants to send a message.

In some embodiments, messaging system 102 may also detect, connect, and/or communicate with other servers, allowing messaging system 102 to route messages to IoT devices, other devices or machines, and/or systems on the other servers via a server-to-server connection. Server-to-server communications may include connections used to transfer data from one server to another server. For example, a user may use multiple cloud servers to store different types of information. A user may want to transfer data from a first server of a first cloud network to a second server of a second cloud network. A server-to-server communication allows the user to directly transfer or otherwise share this information with the second server.

As another example, the messaging system 102 supports inter-cloud communications to allow people, devices or machines, systems, or components thereof to route messages across clouds to other people, devices or machines, systems, or components thereof registered with other clouds. For instance, a device connected to a private or public cloud network may send a message to another device connected to another private or public cloud.

IoT devices, other devices or machines, and/or systems may be able to connect with the messaging system 102 in several ways. In some embodiments, devices and systems may communicate with the messaging system 102 using a messaging system gateway or hub. For example, IoT devices, other devices or machines, and/or systems may communicate with the messaging system 102 using messaging system gateway 114. The messaging system gateway 114 may be connected to a same LAN as the devices that use the messaging system gateway 114. For example, the messaging system gateway 114 may be installed at a location, such as a home, office, a sports venue, an outside environment (e.g., a park, a city, or the like), or any other suitable location.

In some embodiments, the messaging system gateway 114 includes an instance of messaging system software that is configured to interact with the messaging system 102. In some cases, the messaging system gateway 114 may be run on an operating system, such as, but not limited to, Linux, Mac OS, and/or Windows.

In some embodiments, a messaging system gateway 114 may be a standalone physical device, such as a wireless router or modem, which runs the gateway software that connects to the messaging system 102 using a WAN. In some embodiments, a messaging system gateway 114 may be integrated into an IoT device, other device or machine, and/or system by installing the gateway software onto the IoT device, other device or machine, and/or system. For example, the messaging system gateway 114 may be run on computing devices such as a Raspberry Pi, a home and/or office computer, Intel™ Galileo, Beagle Bones, Yuns, and/or other suitable computing device.

Regardless of physical form, the messaging system gateway 114 may operate as an intermediary between the messaging system 102 and the devices or systems that use the messaging system gateway 114. For example, IoT devices, other devices or machines, and/or systems may be connected to messaging system gateway 114, which then links the IoT devices, other devices or machines, and/or systems to the messaging system 102 in real-time.

The connection of a device or system to the messaging system 102 via the messaging system gateway 114 allows connected IoT devices, other devices or machines, and/or systems to communicate with one another in real-time. IoT devices, other devices or machines, and/or systems may be connected to messaging system gateway 114 using one or more native connection protocols of the IoT device, other device or machine, and/or system.

The protocols may include, but are not limited to, Transmission Control Protocol (TCP), User Datagram Protocol (UDP), WiFi, ZigBee, Bluetooth low energy (BLE), HTTP, websockets, MQTT, CoAP, XMPP, SNMP, AllJoyn, and/or any other suitable connection protocol. In some embodiments, messaging system gateway 114 may broadcast a private network signal such that registered devices and systems may securely connect to the messaging system gateway 114 and to the messaging system 102. Devices and systems that do not have access to the messaging system gateway 114 and messaging system 102 may be unable to process the private network signal.

In some embodiments, messaging system gateway 114 is on a LAN side of a firewall, such as a network address translations (NAT) firewall implemented using a router, or other suitable firewall. In some cases, the messaging system gateway 114 may use websockets to connect to the messaging system 102. The connection between websockets of the messaging system gateway 114 and the messaging system 102 may include a bi-directional persistent connection. The bi-directional persistent connection may auto-reconnect as WAN (e.g., Internet, or the like) connectivity becomes available.

By locating the messaging system gateway 114 inside of the firewall, only communications to and from the messaging system gateway 114 have to be granted access to the firewall. Accordingly, the messaging system 102 and any system and/or device connected to the messaging system gateway 114 may communicate through the firewall via the messaging system gateway 114. The messaging system gateway 114 may be used by a person or business to connect various IoT devices, other devices or machines, and/or systems to the messaging system 102, serving as a secure connection for communicating with messaging system 102, much like a personal firewall.

Devices and systems may also be able to communicate with the messaging system 102 using a mobile messaging system gateway that is installed on a mobile device. For example, IoT devices, other devices or machines, and/or systems may be able to connect with the messaging system 102 using a mobile gateway 118. The mobile gateway 118 may be similar to a messaging system gateway 114, but instead is installed and operated on a mobile device. For example, mobile gateway 118 may be installed on a mobile phone, tablet, laptop, wearable device, or other suitable mobile device.

The mobile gateway 118 may allow the mobile phone to connect to the messaging system 102. The mobile gateway 118 may access all sensors on the mobile device. For example, geolocation sensor data, compass headings, accelerometer data, or any other sensor data of a mobile phone may be provided to the messaging system 102 through mobile gateway 118. In some embodiments, the mobile gateway 118 may be installed in wearable technology, such as pedometers, headsets, watches, and the like, as well as in Bluetooth™ low-energy devices.

In some embodiments, the mobile gateway 118 may also provide a personal area network (PAN) and may allow other devices that are connectable to the mobile device to connect to the messaging system 102 via the mobile gateway 118. For example, one or more devices that do not have an Internet Protocol address and that are not able to connect to a LAN (e.g., a WiFi network or the like) may connect to the mobile gateway 118 using a wired interface or a short-range communication protocol interface, such as Bluetooth, BLE, Zigbee, near field communication (NFC), radio frequency (RF), infrared (IR), or any other suitable communication protocol.

These devices may then connect to messaging system 102 through the mobile gateway 118 of the mobile device. The mobile gateway 118 may operate to exchange communications between the devices and the messaging system 102. Devices that do not have an Internet Protocol address and that are not able to connect to a local area network may include wearable technology or other similar devices that only have access to a PAN.

In some embodiments, an IoT device, other device or machine, and/or system may connect with messaging system 102, the messaging system gateway 114, and/or the mobile gateway 118 using a universal messaging system interface 116 that is programmed into the device or system. The built-in universal messaging system interface 116 (or universal interface 116) allows a device or system to perform operations that native firmware of the device or system does not allow it to perform. For example, the messaging system interface 116 may override the native firmware of a device to allow the device to perform various operations that are outside of the functionality of the native firmware.

In some embodiments, the messaging system interface 116 may be installed on a device that does not have the ability to communicate with other devices using one or more connection protocols. In such embodiments, the messaging system interface 116 may provide the device with the capability to use one or more connection protocols. The messaging system interface 116 may access one or more sensors, inputs, outputs, or programs on the device or system in order to perform various operations. For example, the messaging system interface 116 may have access to and control a geolocation sensor, a compass, a camera, a motion sensor, a temperature sensor, an accelerometer, a gyroscope, a graphical interface input, a keypad input, a touchscreen input, a microphone, a siren, a display, a light, a tactile output, a third-party messaging service that the device or system is able to run, or any other component of a device or system that can be identified, accessed, and/or controlled.

In some embodiments, the built-in universal messaging system interface 116 may include an operating system that allows the device to communicate with the messaging system 102. Messaging system interface 116 may be installed on an IoT device, other device or machine, and/or system server. For example, the messaging system interface 116 may be installed on a Raspberry Pi board, an Arduino board, a microcontroller, a minicomputer, or any other suitable computing device.

In some embodiments, a device or system running the messaging system interface 116 may connect directly to messaging system 102. In some embodiments, a device or system running the messaging system interface 116 may connect to the messaging system 102 via the messaging system gateway 114 or the mobile gateway 118. The messaging system interface 116 run by the device or system may be assigned a UUID and a token. The messaging system interface 116 may connect to the messaging system 102 using the assigned UUID and token, and may await further instructions from the messaging system 102.

In some embodiments, the messaging system 102 may act as a compute server that controls the messaging system interface 116. For example, messaging system 102 may activate and/or deactivate pins of the computing device running the messaging system interface 116, request sensor data from the computing device, and/or cause the messaging system interface 116 to perform other functions related to the computing device. In some embodiments, the messaging system interface 116 can be connected to a gateway (e.g., messaging system gateway 114 or mobile gateway 118), and the gateway may act as a computer server that controls the messaging system interface 116 in a similar manner as described above. In some embodiments, messaging system interface 116 may be a mobile operating system or application that is able to run on mobile device operating systems, such as iOS and Android operating systems.

Information obtained by messaging system 102, including information transmitted to messaging system 102 by messaging system gateway 114, mobile gateway 118, messaging system interface 116 and/or directly from an IoT device or system, may be transmitted to one or more data storage systems. For example, information about IoT devices, other devices or machines, and/or systems registered with the messaging system 102 may be transmitted to device directory 104 for storage.

In some embodiments, the information about the IoT device, other device or machine, and/or system may be stored in device directory 104 upon registration of the IoT device, other device or machine, and/or system. For example, information stored in device directory 104 for a device or system may include a unique identifier (e.g., a UUID), a token, information related to when the device or system comes online or offline, a permissions record (described below), a security profile (described below), and/or any other relevant information.

In some embodiments, the device directory 104 is queriable, such that a device, system, or user may be provided with a list and/or array of IoT devices, other devices or machines, and/or systems that fit requested search criteria. The messaging system 102 may access the device directory 104 upon receiving a query from a device, system, or user. Upon polling the device directory 104 according to the criteria specified in a query made by a device, the messaging system 102 may provide the device with a list or array of unique identifiers (e.g., UUIDs) assigned to IoT devices, other devices or machines, and/or systems that are currently online and that the device has access to according to the device's UUID and/or security token.

As described in further detail below, the device's access may be determined using permission records and/or security profiles of the IoT devices, other devices or machines, and/or systems that meet the search criteria of the query. For example, a permissions record operates as a security feature, ensuring that devices, systems, and users only have access to other devices, systems, and users to which permission has been granted.

In some embodiments, sensor data from sensors of registered IoT devices, other devices or machines, and/or systems may be transmitted to sensor data storage 106. The sensor data may be streamed from a registered IoT device, other device or machine, and/or system through messaging system 102 in real-time. Sensor data storage 106 is queriable such that a user, device, or system may poll sensor data storage 106 to receive data from specified sensors during a specified time period.

A user, device, or system may also be able to query the sensor data storage 106 for all available data from one or more sensors. In some embodiments, information from sensor data storage 106, as well as additional information from messaging system 102, may be transmitted to an analytics database 108. In some embodiments, analytics database 108 may not be queried by a user of the system 100. In other embodiments, analytics database 106 may be queried by a user of the system 100. The information stored in analytics database 108 may be accessible via a platform network 110.

In some embodiments, multiple servers or other systems may each operate an instance of software that includes the messaging system 102, thus creating multiple cloud servers and/or instances of messaging systems 102. In some embodiments, a particular instance of messaging system 102 may have its own UUID that allows the instance of messaging system 102 to connect to another instance of messaging system 102 to form a mesh network of messaging systems. Other networks and devices or machines may also be part of the mesh network, such as LANs and PANs and the devices or machines that are interconnected using the LANs and PANs.

Each of the LANs and PANs can have their own unique UUID and/or token registered with the messaging system 102. The LANs and PANs are addressable using their unique UUID, and can also address other UUIDs around the world. Such a mesh network may allow messages and other communications to be routed between devices across messaging systems 102. Accordingly, the messaging system 102 supports inter-cloud communications to allow people, devices or machines, systems, or components thereof to route messages across clouds to other people, devices or machines, systems, or components thereof on other clouds. Each of the cloud networks may run an instance of the messaging system 102. For instance, a device connected to a private or public cloud network may send a message to another device connected to another private or public cloud.

As described above, each person, device or machine, system (e.g., cloud network running an instance of the messaging system, a LAN, a PAN, or the like), or components thereof, that is registered with the messaging system 102 is assigned a UUID. Each person, device or machine, system, or components thereof can be referenced by the messaging system using its UUID. Each of the UUIDs can discover other UUIDs (e.g., clouds, other networks, people, or devices or machines) using one or more queries, such as using multicast Domain Name System (MDNS) or API queries.

In some embodiments, a UUID can connect to multiple networks thus forming a global mesh network including different networks (e.g., multiple cloud networks, LANs, PANs, or a combination of cloud networks, LANs, and/or PANs). A cloud network running an instance of messaging system may also be assigned a UUID and can route messages across cloud networks via inter-cloud communications using a routing paradigm. For example, a cloud network can send a message across cloud networks by sending the message with a route UUID 1/UUID 2/UUID 3/UUID 4, with each UUID being assigned to a different cloud network. In some embodiments, the mesh network may route the message based on known connections.

Platform network 110 may include one or more analytics engines that may process the information received from the analytics database 108. The analytics engines may aggregate the received information, detect trends, and/or perform other analytics on the information. Platform network 110 may be communicatively coupled with a number of APIs 112 that are used to create, manage, identify, and/or communicate with functions of different IoT devices, other devices or machines, and/or systems.

APIs may include, for example, sales analytics APIs, social media account and other third-party messaging account APIs, stock quote APIs, weather service APIs, other data APIs, mobile application APIs, and any other suitable API. For example, a Facebook™ or other social media message may use a messaging API to send SMS messages. Platform network 110 may use the messaging API to deliver a message to a device or system configured to display a SMS message.

A light API may be provided by a manufacturer of "smart" light bulbs. The platform network 110 may utilize the light API to provide an output to turn a light bulb connected to the platform network 110 on or off. Platform network 110 is also in communication with messaging system 102 using the APIs of messaging system 102. Platform network 110 may interact with the IoT devices, other devices or machines, and/or systems connected through the messaging system 102 using UUIDs and/or security tokens.

The UUIDs and/or security tokens may be issued by the messaging system 102 and/or the platform network 110. In some embodiments, a user may register systems and/or devices with the messaging system 102. The platform network 110 may import or otherwise utilize any UUIDs and/or tokens issued by the messaging system 102 during the registration. In some embodiments, a user may register devices and/or systems with the platform network 110.

The platform network 110 may issue UUIDs and security tokens to IoT devices, other devices or machines, and/or systems upon registration of the IoT device, other device or machine, and/or system. The UUIDs and security tokens are used to access the messaging system 102, as described above. In some embodiments, a user may register devices and/or systems with both the messaging system 102 and the platform network 110. Either messaging system 102 or platform network 110 may issue UUIDs and/or tokens. Registration with the non-issuing system or network creates a link or other association with the issued UUIDs and/or security tokens.

Platform network 110 may operate an application or other program that provides a designer graphical interface that allows a user to create a control system or flow. The designer graphical interface may allow the user to create a control system by dragging and dropping blocks that represent various devices and/or systems of the control system, blocks that represent inputs and/or outputs from the various devices and/or systems, and/or blocks that represent functions for controlling the devices and/or systems.

Any IoT device, other device or machine, and/or system that is registered with platform network 110 may be configured to receive or transmit a message to any other IoT device, other device or machine, and/or system that is registered with platform network 110 using an appropriate control system designed using the designer graphical interface. Messages may be transmitted from one device or system to control operation of another device or system. For example, the platform network 110 may run control systems continuously, such that an input from a device or system may automatically cause an event to occur in a different location and/or by a different device or system.

Such functionality, along with access to the data from analytics database 108, enables the platform network 110 to monitor a performance, behavior, and/or state of any IoT device, other device or machine, and/or system within the control system, and to send a resulting message or communication to any other IoT device, other device or machine, and/or system in the control system based on the monitored performance, behavior, and/or state. In another example, the platform network 110 may run a control system designed using the designer graphical interface upon receiving a command, such as from a user or from another device or system.

In some embodiments, the designer graphical interface operated by the platform network 110 may access any IoT device, other device or machine, and/or system connected to messaging system 102, including IoT devices, other devices or machines, and/or systems connected using the messaging system gateway 114, messaging system interface 116, and/or mobile gateway 118. This connection enables control systems created using the designer graphical interface to control output functions of devices and/or systems registered with the messaging system 102. For example, real-time monitoring of data at a remote location, such as performance of a machine or system, or of a person's health condition may be performed by the platform network 110.

The platform network 110 may also automatically provide messages or other outputs, including commands, to any of the registered IoT devices, other devices or machines, and/or systems based on processes performed on information received from IoT devices, other device or machine, and/or system. For example, sensor data may be received from an IoT device and processed by analytics systems of the platform network 110. Using artificial intelligence and/or machine learning within the platform network 110, the processed sensor data may be used to provide commands to another system or device connected to platform network 110.

Figure 2:
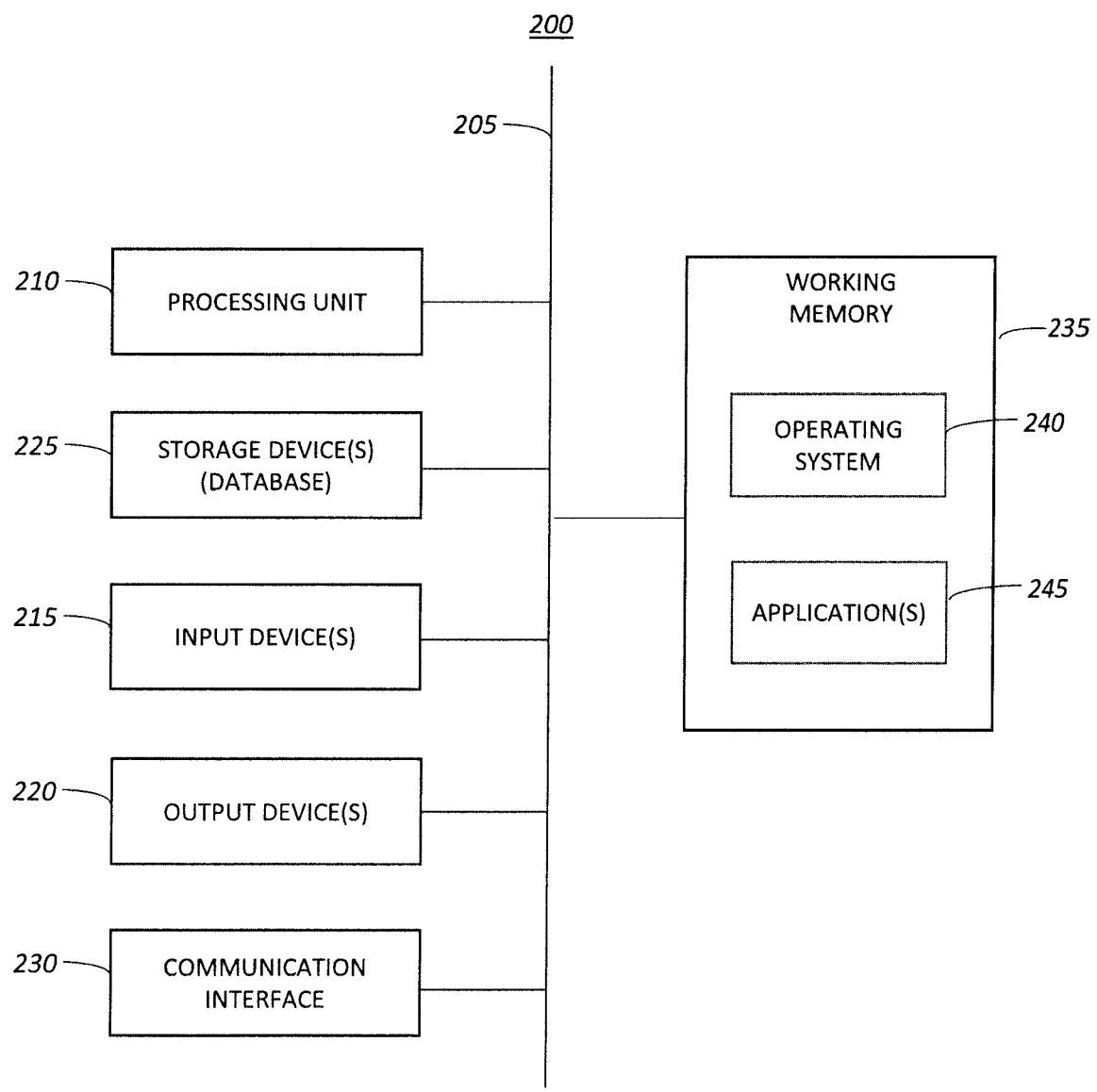
FIG. 2 is a block diagram of a computer system representing one or more of the components of the system illustrated in FIG. 1.

Referring now to FIG. 2, a computer system representing one or more of the components of the messaging system 102, the platform network 108, the messaging system gateway 114, the messaging system interface 116, or the mobile gateway 118 will be discussed.

FIG. 2 provides a schematic illustration of one embodiment of a computer system 200 that can perform the methods provided by various other embodiments, as described herein, and/or can function as the host computer system, a remote kiosk/terminal, a point-of-sale device, a mobile device, and/or a computer system. FIG. 2 is meant only to provide a generalized illustration of various components, any or all of which may be utilized as appropriate. FIG. 2, therefore, broadly illustrates how individual system elements may be implemented in a relatively separated or relatively more integrated manner.

The computer system 200 is shown comprising hardware elements that can be electrically coupled via a bus 205 (or may otherwise be in communication, as appropriate). The hardware elements may include a processing unit 210, including without limitation one or more general-purpose processors and/or one or more special-purpose processors (such as digital signal processing chips, graphics acceleration processors, or other appropriate data processor); one or more input devices 215, which can include without limitation a mouse, a keyboard, a touchscreen, a global positioning system (GPS) receiver, a motion sensor, a camera, and/or the like; and one or more output devices 220, which can include without limitation a display device, a speaker, a printer, and/or the like.

The computer system 200 may further include (and/or be in communication with) one or more non-transitory computer-readable storage mediums or devices 225, which can comprise, without limitation, local and/or network accessible storage, and/or can include, without limitation, a disk drive, a drive array, an optical storage device, a solid-state storage device such as a random access memory ("RAM") and/or a read-only memory ("ROM"), which can be programmable, flash-updateable and/or the like. Such storage devices may be configured to implement any appropriate data stores, including without limitation, various file systems, database structures, and/or the like.

The computer system 200 might also include a communication interface 230, which can include without limitation a modem, a network card (wireless or wired), an infrared communication device, a wireless communication device and/or chipset (such as a Bluetooth™ device, an 802.11 device, a WiFi device, a WiMax device, an NFC device, cellular communication facilities, etc.), and/or similar communication interfaces. The communication interface 230 may permit data to be exchanged with a network (such as the network described below, to name one example), other computer systems, and/or any other devices described herein.

In many embodiments, the computer system 200 will further comprise a non-transitory working memory 235, which can include a RAM or ROM device, as described above. The computer system 200 may further include one or more receivers and one or more transmitters. For example, the communication interface 230 may include one or more receivers and one or more transmitters. In another example, the computer system 200 may include one or more transceivers, one or more receivers, and/or one or more transmitters that are separate from the communication interface 230.

The computer system 200 also can comprise software elements, shown as being currently located within the working memory 235, including an operating system 240, device drivers, executable libraries, and/or other code, such as one or more application programs 245, which may comprise computer programs provided by various embodiments, and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be stored on a computer-readable storage medium, such as the one or more non-transitory computer-readable storage mediums or devices 225 described above. In some cases, the storage medium might be incorporated within a computer system, such as computer system 200, In other embodiments, the storage medium might be separate from a computer system (e.g., a removable medium, such as a compact disc), and/or provided in an installation package, such that the storage medium can be used to program, configure and/or adapt a general purpose computer with the instructions/code stored thereon. These instructions might take the form of executable code, which is executable by the computer system 200 and/or might take the form of source and/or installable code, which, upon compilation and/or installation on the computer system 200 (e.g., using any of a variety of generally available compilers, installation programs, compression/decompression utilities, etc.) then takes the form of executable code.

In some examples, a receiver of the computer system 200 may receive a communication from a first Internet of Things (IoT) device, wherein the communication is destined for a second IoT device, wherein the first IoT device is assigned a first universally unique identifier, and wherein the communication includes a second universally unique identifier assigned to the second IoT device. In such examples, the one or more non-transitory computer-readable storage mediums or devices 225 may contain instructions which when executed on the one or more data processors, cause the one or more processors to perform operations including obtaining the second universally unique identifier, determining that the second universally unique identifier is assigned to the second IoT device, and determining, using the second universally unique identifier, that the communication received from the first IoT device is an unauthorized message attempt by the first IoT device to exchange a message with the second IoT device.

Substantial variations may be made in accordance with specific requirements. For example, customized hardware might also be used, and/or particular elements might be implemented in hardware, software (including portable software, such as applets, etc.), or both. Moreover, hardware and/or software components that provide certain functionality can comprise a dedicated system (having specialized components) or may be part of a more generic system.

For example, a journey planning and pricing engine configured to provide some or all of the features described herein relating to the journey planning and/or pricing can comprise hardware and/or software that is specialized (e.g., an application-specific integrated circuit (ASIC), a software method, etc.) or generic (e.g., processing unit 210, applications 245, etc.) Further, connection to other computing devices such as network input/output devices may be employed.

Some embodiments may employ a computer system (such as the computer system 200) to perform methods in accordance with the disclosure. For example, some or all of the procedures of the described methods may be performed by the computer system 200 in response to processing unit 210 executing one or more sequences of one or more instructions (which might be incorporated into the operating system 240 and/or other code, such as an application program 245) contained in the working memory 235. Such instructions may be read into the working memory 235 from another computer-readable medium, such as one or more of the storage device(s) 225. Merely by way of example, execution of the sequences of instructions contained in the working memory 235 might cause the processing unit 210 to perform one or more procedures of the methods described herein.

In an embodiment implemented using the computer system 200, various computer-readable storage media might be involved in providing instructions/code to processing unit 210 for execution and/or might be used to store and/or carry such instructions/code (e.g., as signals). In many implementations, a computer-readable storage medium is a physical and/or tangible storage medium. Such a medium may take many forms, including but not limited to, non-volatile media, volatile media, and transmission media.

Non-volatile media include, for example, optical and/or magnetic disks, such as the storage device(s) 225. Volatile media include, without limitation, dynamic memory, such as the working memory 235. Transmission media include, without limitation, coaxial cables, copper wire and fiber optics, including the wires that comprise the bus 205, as well as the various components of the communication interface 230 (and/or the media by which the communication interface 230 provides communication with other devices). Hence, transmission media can also take the form of waves (including without limitation radio, acoustic and/or light waves, such as those generated during radio-wave and infrared data communications).

Common forms of physical and/or tangible computer-readable media include, for example, a magnetic medium, optical medium, or any other physical medium with patterns of holes, a RAM, a PROM, EPROM, a FLASH-EPROM, any other memory chip or cartridge, a carrier wave as described hereinafter, or any other medium from which a computer can read instructions and/or code.

The communication interface 230 (and/or components thereof) generally will receive the signals, and the bus 205 then might carry the signals (and/or the data, instructions, etc. carried by the signals) to the working memory 235, from which the processor(s) 205 retrieves and executes the instructions. The instructions received by the working memory 235 may optionally be stored on a non-transitory storage device 225 either before or after execution by the processing unit 210.

Figure 3:
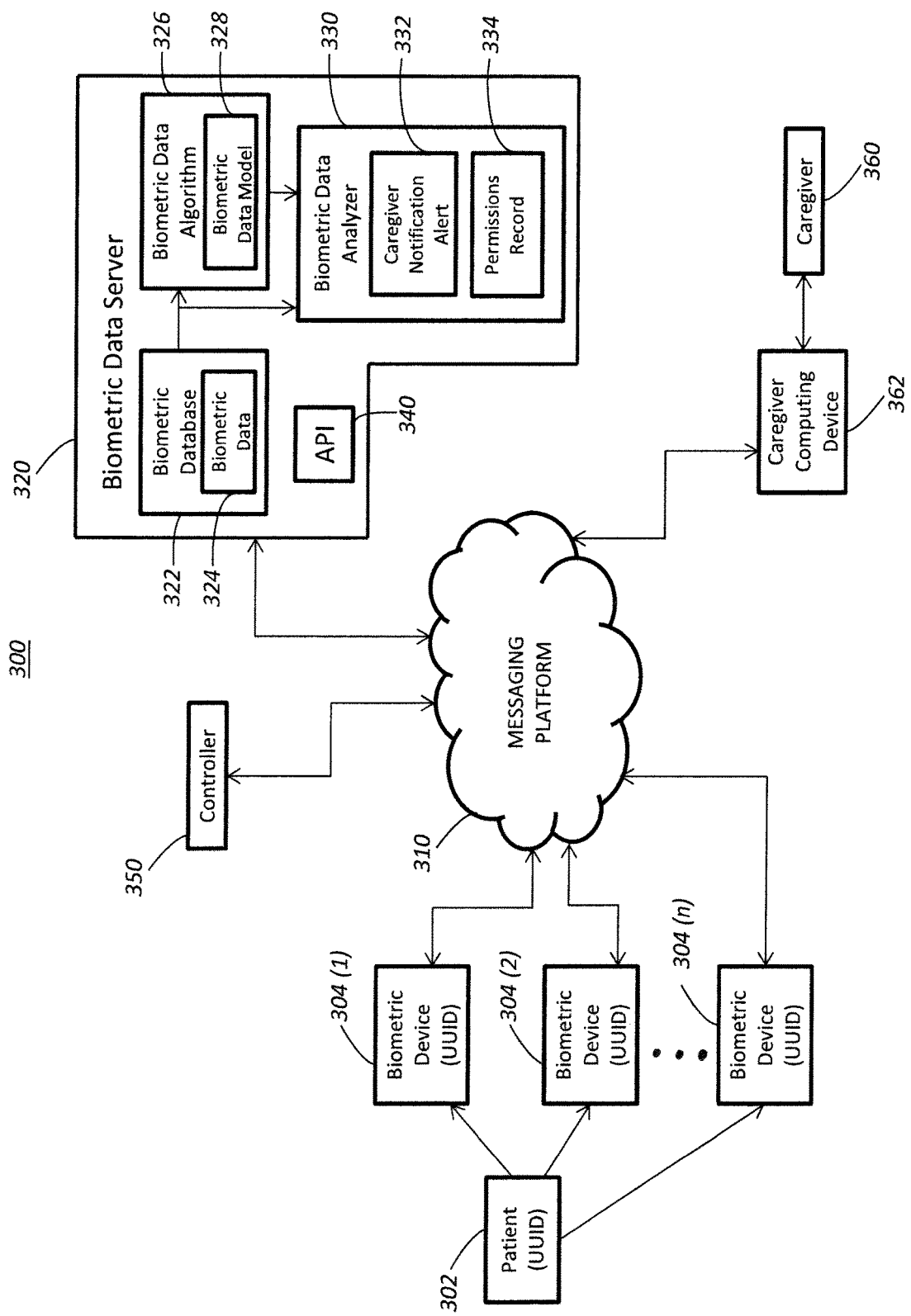
FIG. 3 is a block diagram of a cloud-based distributed healthcare system that aggregates and analyzes biometric data from disparate biometric devices.

Referring now to FIG. 3, another aspect of the disclosure is directed to a cloud-based distributed healthcare system 300 that aggregates and analyzes biometric data 324 from disparate biometric devices 304(1)-304(n). The system 300 includes biometric devices 304(1)-304(n) generating biometric data on a person 302. The person 302 may also be referred to as a patient. The biometric devices 304(1)-304(n) transmit the biometric data 324 via respective messaging protocols.

A messaging platform 310 receives the biometric data 324 from the biometric devices 304(1)-304(n) based on the respective messaging protocols. A biometric data server 320 receives the biometric data 324 from the messaging platform 310. The biometric data server 320 includes a biometric database 322, a biometric data algorithm 326, and a biometric data analyzer 330.

The biometric database 322 stores the biometric data 324 from the biometric devices 304(1)-304(n). The biometric data algorithm 326 generates a biometric data model 328 over time based on the biometric data to determine the person's version of normal bio-feedback at any given time in comparison to other like time periods. The biometric data analyzer 330 analyzes new biometric data 324 in view of the biometric data model, and generates a caregiver alert notification 332 when an anomaly is detected outside a range of the biometric data model 328.

The biometric devices are generally indicated by reference 304 while specific biometric devices in the illustrated embodiment are addressed by references 304(1)-304(n). The biometric devices 304 are based on wearable technology carried by the person 302.

The biometric devices 304 may also be referred to as IoT devices as discussed above. The biometric devices 304 include blood sugar monitors, thermometers, heart-rate monitors, body metric scales, pulse oximeters, pedometers, and blood-pressure monitors to name a few. As readily appreciated by those skilled in the art, this list of biometric devices 304 is an example of such devices and is not to be limiting. The biometric data from each of the biometric devices 304 may be streamed in real time to the biometric database 322.

The cloud-based distributed healthcare system 300 advantageously collects and aggregates a variety of bio-feedback data from a variety of disparate biometric devices 304 and stores the bio-feedback data 324 in a biometric database 322 within the biometric data server 320 that is capable of conducting real-time, cross-system diagnostics. The biometric data algorithm 326 advantageously determines each person's version of normal bio-feedbacks, predicts the onset of healthcare conditions and/or issues based on the biometric data model 328, and alerts caregivers 360 of anomalies.

Anyone of the biometric devices 304 may be operating with a messaging protocol that is different from the other biometric devices 304. The biometric devices 304 collectively interface with the messaging platform 310 which is made up of individual messaging platforms (i.e., IoT messaging platforms). Each messaging platform supports a particular messaging or connection protocol.

The messaging or connection protocols may include a HTTP connection protocol, a websockets connection protocol, a MQTT connection protocol, a CoAP connection protocol, an AMQP connection protocol, an XMPP connection protocol, a SNMP connection protocol, an AllJoyn connection protocol, or any other appropriate connection protocol.

One of ordinary skill in the art will recognize that the messaging platform 310 may operate using any other appropriate machine-to-machine connection protocol. Other protocols may be added to the messaging platform 310 over time as the protocols become more universally used. As discussed above in FIG. 1, the messaging platform 310 is a cross-protocol, machine-to-machine messaging platform. An example messaging platform is Meshblu by Citrix Octoblu.

The biometric data server 320 may be cloud based, for example, and is configured to interface with the different biometric devices 304(1)-304(n) via the messaging platform 310. A controller 350 is used to register the person 302, the biometric devices 304, the caregiver 360, and a caregiver computing device 362 with the messaging platform. The caregiver computing device 362 may be a mobile phone, tablet, laptop, or other suitable computing device, for example.

The controller 350 also interfaces with an API 340 within the biometric database server 320. The controller 350 may be a fixed device, such as an Arduino Uno micro-controller, for example. Alternatively, the controller 350 may be a mobile device.

Upon registration, the person 302, each biometric device 304, the caregiver 360 and the at least one caregiver computing device 362 are assigned a respective universal unique identifier (UUID). The person's UUID and the caregiver's UUID are used to ensure HIPPA compliance.

The biometric data 324 transmitted by the biometric devices 304 is encrypted via a transport layer security (TLS)/secure sockets layer (SSL). In addition, the message payload data portion of the biometric date 324 may be encrypted with public/private keys. The biometric devices 304 are thus capable of securely streaming device-agnostic bio-feedback data 324 to the biometric data server 320.

The biometric devices 304 are device agnostic in the sense that the biometric data algorithm 326 can process the biometric data 324 without requiring any special adaptations. The biometric devices 304 are compatible across most common systems.

As the biometric data is stored in the biometric database 322, it is transformed to a common data structure. This advantageously allows the biometric data algorithm 328 and the biometric data analyzer 330 to model and analyze the stored biometric data 324 in a consistent manner regardless of any particular biometric device being used by the patient 302.

Multiple devices from different manufacturers may be selected for use by the patient 302. Storing the biometric data 324 using a common data structure regardless of the device manufacturer insures that such data is consistently handled by the biometric data server 320.

For example, biometric data provided by a blood glucose meter may be in different units. The international standard way of measuring blood glucose levels are in terms of a molar concentration, measured in mmol/L (millimoles per litre; or millimolar, abbreviated mM). In the United States, West-Germany and other countries mass concentration is measured in mg/dL (milligrams per decilitre). Consequently, a determination is made ahead of time to store all measured blood glucose levels in the same units, such as mg/dL. If blood glucose levels were received in mM, then this would be converted to mg/dL prior to storage in the database 322 so as to have a common data structure for all measured blood glucose levels.

Similarly, all temperature data provided by thermometers would be stored using the same temperature scale, such as Fahrenheit instead of Celsius, for example. As another example, biometric data from body metric scales weight would be stored using the same weight scale, such as pounds instead of kilograms, for example.

The biometric data algorithm 326 builds over time a biometric data model 328 based on the received biometric data 324. The time period is long enough to build a model of patient data to determine a patient's version of normal bio-feedback at any given time in comparison to other like periods. The time period may be weeks or months, for example. As one skilled in the art readily understands, the accuracy of the biometric data model 328 is improved the longer a patient's biometric data 324 is collected in order to refine the model.

The biometric data model 328, for example, may include the patient's blood glucose levels. The patient's blood glucose level is modeled to provide a regular pattern of blood glucose levels as well as a regular pattern of variations in those levels. When new blood glucose levels are received they are compared to the modeled levels as determined by the biometric data model 328. Any variations could be attributed to the patient's habit or routine of normal daily activities, such as around meal times.

The biometric data 324 provided by the other biometric devices 304 would also be included in the biometric data model 328. The biometric data model 328, for example, may include the patient's heart rate as provided by a heart-rate monitor. The patient's heart rate is modeled to provide a regular pattern of heart rate levels as well as a regular pattern of variations in those levels. The variations could be attributed to the patient's habit or routine of normal daily activities, such as a regular exercise routine.

The biometric data 324 stored in the biometric database 322 may be referred to as big data. Big data includes very large data sets that may be analyzed computationally to reveal patterns, trends, and associations, especially relating to human behavior and interactions.

The biometric data analyzer 330 and the biometric data algorithm 326 are shown separate from one another. Alternatively, the function of the biometric data analyzer 330 may be included as part of the biometric data algorithm 326, as readily appreciated by those skilled in the art. This is particularly so when the biometric data algorithm 326 is a machine learning algorithm.

A machine learning algorithm makes predictions or calculated suggestions based on large amounts of data. As readily understood by those skilled in the art, machine learning algorithms can be divided into three broad categories: supervised learning, unsupervised learning, and reinforcement learning.

Supervised learning is useful in cases where a property (label) is available for a certain dataset (training set), but is missing and needs to be predicted for other instances. Unsupervised learning is useful in cases where the challenge is to discover implicit relationships in a given unlabeled dataset (items are not preassigned). Reinforcement learning falls between these 2 extremes. There is some form of feedback available for each predictive step or action, but no precise label or error message.

The biometric data algorithm 326 for the illustrated cloud-based distributed healthcare system 300 is based on at least one of the above described three categories, such as supervised learning. Once the biometric data model 328 has been built, then the biometric data analyzer 330 examines the patient's version of normal bio-feedback at any given time in comparison to other like time periods when new biometric data is received to look for any anomalies detected outside of the model. Any anomalies detected outside of the model will trigger a caregiver notification alert 332 to be transmitted to a caregiver 360. The caregiver 360 may be a family member or a physician, for example.

For illustration purposes, the patient's normal heart rate may be about 70 beats per minute, but during a heart attack, this rate is altered due to the disrupted blood flow. Heart rates during a heart attack can vary from too slow or too fast to palpitations and even skipped beats. Location of the blockage in the heart often has a direct correlation on the type of heart rate.

If the biometric data analyzer 330 determines that the patient's heart rate is too fast, and the heart rate is outside the upper boundaries of the biometric data model 328, then the patient may be experiencing a heart attack. In this case, the biometric data analyzer 330 generates the caregiver notification alert 332. Similarly, if the biometric data analyzer 330 determines that the patient's heart rate is too slow, and the heart rate is outside of the lower boundaries of the biometric data model 328, then the patient may still be experiencing a heart attack. In this case, the biometric data analyzer 330 also generates the caregiver notification alert 332. In this example, the biometric data analyzer 330 would also monitor the model 328 for anomalies with respect to palpitations and even skipped beats.

In addition, the biometric data algorithm 326 may be used to predict the onset of healthcare conditions and/or issues based on a patient's version of normal bio-feedbacks compared to the rest of their biometric data 324 stored in the system 300. The biometric data algorithm 326 is further configured to look for patterns related to undiagnosed similar symptoms.

For instance, assume that the patient's blood sugar is not being monitored but the biometric data analyzer 330 determines that the patient has a faster than normal heartbeat around meal times. Low blood sugar may be a cause of the faster than normal heartbeat but after the patient eats then the heart rate returns to normal as the blood sugar levels increase. The biometric data analyzer 330 in combination with the biometric data algorithm 326 is further configured to look for patterns related to undiagnosed similar symptoms. In this case, a caregiver 360 receives a caregiver notification alert 332, where the caregiver could then receive information about the patient possibly having low blood sugar levels.

As noted above, the caregiver 360 could be a family member or physician, for example. The caregiver notification alert 332 may be sent to one or more of these individuals based on a permissions record 334 associated with the patient 302 and the biometric devices 304 generating biometric data on the patient.

The permissions record 334 ensures that certain individuals will receive the caregiver notification alerts 332, which then allows them to receive the biometric data being generated by one or more of the biometric devices 304. In addition, permissions record 334 may further limit which data is available to which individuals.

A cardiologist physician, for example, receiving a caregiver notification alert 332 may only have access to the biometric data being generated by the heart rate monitor. Such data may be received by the cardiologist physician in real time.

Similarly, a diabetes physician, for example, receiving a caregiver notification alert 332 may only have access to the biometric data being generated by the blood glucose meter. Such data may be received by the diabetes physician in real time.

Alternatively, or in addition to the above scenarios, the patient's primary care doctor may be authorized by the permissions records 334 to receive all of the caregiver notification alerts 332. In this case the primary care physician would also be able to receive all of the generated biometric data in real time as needed.

Each caregiver and physician are registered with the cloud-based distributed healthcare system 300 so as to comply with HIPPA laws. Each caregiver and physician would have their own permissions record. Registration involves each caregiver and physician receiving an assigned UUID. Additional implementation of the permissions record 334 may be found in U.S. Pat. No. 9,094,407. The '407 patent is assigned to the current assignee of the present application, and is incorporated herein by reference in its entirety.

Figure 4:
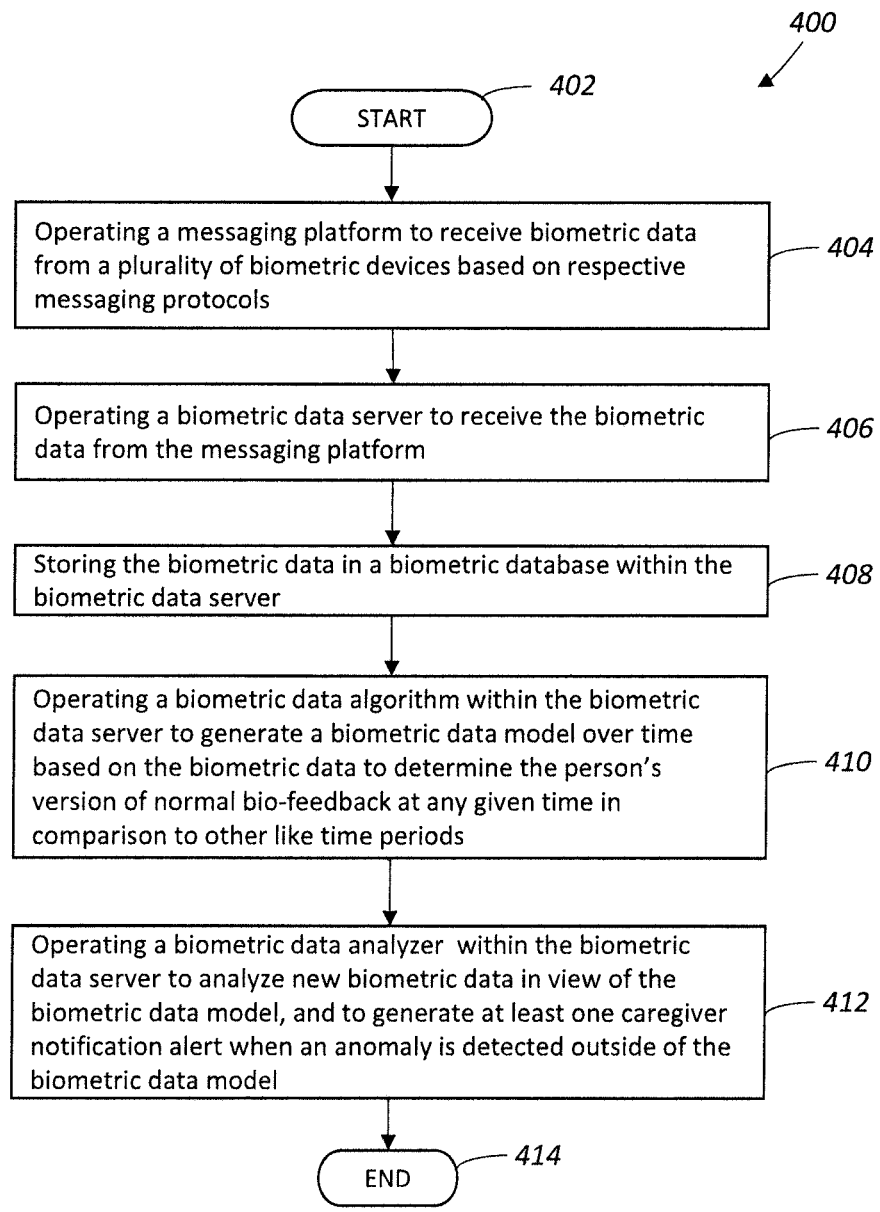
FIG. 4 is a flowchart illustrating a method for operating the cloud-based distributed healthcare system illustrated in FIG. 3.

Another aspect is directed to a method for operating the cloud-based distributed healthcare system 300 as described. Referring to the flowchart 400 in FIG. 4, the method comprises from the start (Block 402), operating a messaging platform 310 to receive the biometric data 324 from the plurality of biometric devices 304 based on the respective messaging protocols at Block 404, and operating a biometric data server 320 to receive the biometric data 324 from the messaging platform 310 at Block 406. Operating the biometric data server 320 includes storing the biometric data 324 at Block 408, operating a biometric data algorithm 410 at Block 410 to generate a biometric data model 328 over time based on the biometric data 324 to determine the person's version of normal bio-feedback at any given time in comparison to other like time periods, and analyze new biometric data 324 in view of the biometric data model 328 and generate at least one caregiver notification alert 332 when an anomaly is detected outside the biometric data model 328 at Block 412. The method ends at Block 412.

Yet another aspect is directed to a non-transitory computer readable medium for a cloud-based distributed healthcare system 300 as described above. The non-transitory computer readable medium has a plurality of computer executable instructions for causing the system 300 to perform steps comprising operating a biometric data server 320 to store the biometric data 324 in a biometric database 322, generate a biometric data model 328 over time based on the biometric data 324 to determine the person's version of normal bio-feedback at any given time in comparison to other like time periods, and analyze new biometric data 324 in view of the biometric data model 328 and generate at least one caregiver notification alert 332 when an anomaly is detected outside the biometric data model 328.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the foregoing description.

That which is claimed:

1. A system comprising:
a plurality of biometric devices generating biometric data on a person, with the biometric data corresponding to measured biometric levels and with said plurality of biometric devices transmitting the biometric data via respective messaging protocols;
a messaging platform configured to receive the biometric data from said plurality of biometric devices based on the respective messaging protocols;
a biometric data server configured to receive the biometric data from said messaging platform, said biometric data server comprising
a biometric database to store the biometric data,
a biometric data algorithm to generate a biometric data model over time based on the biometric data to provide regular patterns of the measured biometric levels as well as regular patterns of variations in the measured biometric levels to determine the person's version of normal bio-feedback at any given time in comparison to other like time periods, with the measured biometric levels corresponding to diagnosed symptoms for the person, and a biometric data analyzer to perform the following:
analyze new biometric data in view of the biometric data model,
generate at least one caregiver notification alert when an anomaly is detected outside the biometric data model, and
predict onset of healthcare conditions by looking for patterns related to undiagnosed similar symptoms;
a plurality of different application programming interfaces (APIs) configured to manage functions of different biometric devices; and
said messaging platform further configured to interact with said plurality of different APIs, and to transmit a single message to multiple biometric devices having different APIs associated therewith.

2. The system according to claim 1 wherein said biometric data server is further configured to generate at least one permissions record identifying at least one caregiver allowed to receive the at least one caregiver notification alert.

3. The system according to claim 2 wherein the at least one caregiver has limited access to the biometric data based on the at least one permissions record.

4. The system according to claim 1 further comprising a controller to register the person, said plurality of biometric devices and at least one caregiver computing device with said messaging platform, with the person, each biometric device and said at least one caregiver computing device being assigned a respective universal unique identifier (UUID) upon registration.

5. The system according to claim 4 wherein said biometric data server is further configured to transmit to said at least one caregiver computing device the biometric data from at least one of said plurality of biometric devices.

6. The system according to claim 5 wherein the biometric data is transmitted in real time.

7. The system according to claim 1 wherein each biometric device is configured as an Internet of Thing (IoT) device.

8. The system according to claim 1 wherein said biometric data algorithm comprises a machine learning algorithm.

9. The system according to claim 1 wherein the biometric data is encrypted before being transmitted.

10. A method for operating a system comprising a plurality of biometric devices generating biometric data on a person, with the plurality of biometric devices transmitting the biometric data via respective messaging protocols, with the biometric data corresponding to measured biometric levels, the method comprising:
operating a messaging platform to receive the biometric data from the plurality of biometric devices based on the respective messaging protocols;
operating a biometric data server to receive the biometric data from the messaging platform and to
store the biometric data within the biometric database,
operate a biometric data algorithm within the biometric database to generate a biometric data model over time based on the biometric data to provide regular patterns of the measured biometric levels as well as regular patterns of variations in the measured biometric levels to determine the person's version of normal bio-feedback at any given time in comparison to other like time periods, with the measured biometric levels corresponding to diagnosed symptoms for the person, and
operate a biometric data analyzer within the biometric database to perform the following:
analyze new biometric data in view of the biometric data model,
generate at least one caregiver notification alert when an anomaly is detected outside the biometric data model, and
predict onset of healthcare conditions by looking for patterns related to undiagnosed similar symptoms;
operating a plurality of different application programming interfaces (APIs) to manage functions of different biometric devices; and
operating the messaging platform further to interact with the plurality of different APIs, and to transmit a single message to multiple biometric devices having different APIs associated therewith.

11. The method according to claim 10 further comprising operating the biometric data server to generate at least one permissions record identifying at least one caregiver allowed to receive the at least one caregiver notification alert.

12. The method according to claim 11 wherein the at least one caregiver has limited access to the biometric data based on the at least one permissions record.

13. The method according to claim 10 wherein the system further comprises a controller to register the person, the plurality of biometric devices and at least one caregiver computing device with the messaging platform, with the person, each biometric device and the at least one caregiver computing device being assigned a respective universal unique identifier (UUID) upon registration.

14. The method according to claim 13 further comprising operating the biometric data server to transmit to the at least one caregiver computing device the biometric data from at least one of the plurality of biometric devices.

15. The method according to claim 10 wherein the biometric data algorithm comprises a machine learning algorithm.

16. The method according to claim 10 further comprising encrypting the biometric data before transmitted.

17. A non-transitory computer readable medium for a system comprising a plurality of biometric devices generating biometric data on a person, with the biometric data corresponding to measured biometric levels, and with the plurality of biometric devices transmitting the biometric data via respective messaging protocols; a plurality of different application programming interfaces (APIs) to manage functions of different biometric devices; and a messaging platform to receive the biometric data from the plurality of biometric devices based on the respective messaging protocols, and to interact with the plurality of different APIs, and to transmit a single message to multiple biometric devices having different APIs associated therewith, the non-transitory computer readable medium having a plurality of computer executable instructions for causing the system to perform steps comprising:
operating a biometric data server to perform the following:
store the biometric data in a biometric database,
generate a biometric data model over time based on the biometric data to provide regular patterns of the measured biometric levels as well as regular patterns of variations in the measured biometric levels to determine the person's version of normal bio-feedback at any given time in comparison to other like time periods, with the measured biometric levels corresponding to diagnosed symptoms for the person,
analyze new biometric data in view of the biometric data model, generate at least one caregiver notification alert when an anomaly is detected outside the biometric data model, and predict onset of healthcare conditions by looking for patterns related to undiagnosed similar symptoms.

18. The non-transitory computer readable medium according to claim 17 further comprising operating the biometric data server to generate at least one permissions record identifying at least one caregiver allowed to receive the at least one caregiver notification alert.

19. The non-transitory computer readable medium according to claim 18 wherein the at least one caregiver has limited access to the biometric data based on the at least one permissions record.

20. The system according to claim 1 wherein said biometric database stores the biometric data using a common data structure.

21. The method according to claim 10 wherein the biometric database stores the biometric data using a common data structure.

22. The non-transitory computer readable medium according to claim 17 wherein the biometric database stores the biometric data using a common data structure.

* * * * *